(12) United States Patent
Ho et al.

(10) Patent No.: US 7,544,847 B1
(45) Date of Patent: Jun. 9, 2009

(54) METHOD FOR PRODUCING 1,4-BIS (DICHLOROMETHYL) TETRAFLUOROBENZENE

(75) Inventors: Chan-Yuan Ho, Hsinchu (TW); Tsair-Feng Lin, Bade (TW); Chun-Hsu Lin, Taipei (TW); Shieh-Jun Wang, Taipei (TW)

(73) Assignees: Yuan-Shin Materials Technology Corp., Taipei (TW); Chun-Shan Institute of Science and Technology Araments Bureau, M.N.D., Taoyuan (TW)

( * ) Notice: Subject to any disclaimer, the term of this patent is extended or adjusted under 35 U.S.C. 154(b) by 0 days.

(21) Appl. No.: 12/285,645

(22) Filed: Oct. 10, 2008

(30) Foreign Application Priority Data

Dec. 28, 2007 (TW) ............................. 96150781 A

(51) Int. Cl.
*C07C 17/00* (2006.01)

(52) U.S. Cl. ....................................... 570/207; 570/201
(58) Field of Classification Search ................ 570/201, 570/207

See application file for complete search history.

(56) References Cited

OTHER PUBLICATIONS

Kiktuchi et al., Journal of the American Chemical Society, 126 (21), 6526-6527.*

* cited by examiner

*Primary Examiner*—Jafar Parsa
(74) *Attorney, Agent, or Firm*—Bacon & Thomas, PLLC

(57) ABSTRACT

A method for producing 1,4-bis(dichloromethyl)tetrafluorobenzene is disclosed, which is achieved by reacting tetrafluoroterephthaldehyde, $SOCl_2$ and organic solvents. In the synthesis of 1,4-bis(dichloromethyl)-tetrafluorobenzene by adding formamides as catalyst, there are remarkable advantages which include shortening the reaction time; simplifying the synthesizing steps and raising the yield of the product.

16 Claims, No Drawings

METHOD FOR PRODUCING 1,4-BIS(DICHLOROMETHYL) TETRAFLUOROBENZENE

BACKGROUND OF THE INVENTION

1. Field of the Invention

The present invention relates to a method for producing 1,4-bis(dichloromethyl)tetrafluorobenzene (DCMTFB) and, more particularly, to a method for producing high-yield 1,4-bis(dichloromethyl)tetrafluorobenzene in mass production.

2. Description of Related Art

Parylene polymers possess numerous advantages for manufacturing purposes. For example, the coating environment is at room temperature; no residual stress exists after coating; and precise controls are allowed on the thickness of the deposition film. Additionally, parylene polymer films have advantages such as uniformity, excellent acid and alkali resistance, high transparency and low dielectric constant. Therefore, they have been widely employed in electric insulation on printing circuit boards, damp-proofing on sensors or medical instruments, and anti-corrosion on metal-coating, etc. Presently, the fluoro parylene polymers, for their low dielectric constant and high melting point, can be utilized on dielectric coating in the electrical and coating industries and have become the focus of the attention.

One of fluoro parylene polymers, for example, poly(tetrafluoro-p-xylene) has the structure represented by the following Formula (1).

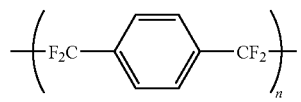

Formula (1)

Fluoro parylene polymers are generally coated on products by means of chemical vapor deposition in a vacuum at room temperature. Products coated with fluoro parylene polymers not only possess excellent anticorrosive, damp-proofing and insulating characteristics, but also have the advantages of extra thinness, transparency and being poreless. By polymerizing active monomers on the object surfaces, fluoro parylene polymer coatings can be formed. Unlike the general steps of liquid coating process, there is another coating process to have the parylene dimers vaporized first, and as the dimer bonds are cleaved to yield monomer free radicals at a pyrolysis condition, the monomer free radicals are polymerized to form parylene polymers.

Currently, the dimer of fluoro parylene polymers often used in the industry is octafluoro-2,2-paracyclophane represented by the following Formula (2).

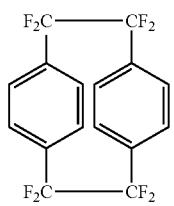

Formula (2)

The dielectric constant of fluoro parylene polymers decreases as the number of fluorine atoms increases within the polymers. Thus, it can be predicted that the parylene polymers polymerized from the dimer of fluoro parylene polymers, represented by the following Formula (3) and containing no hydrogen atoms, can have a lower dielectric constant.

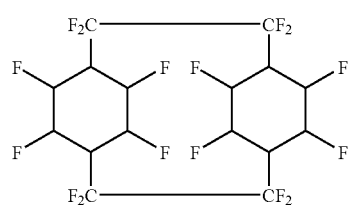

Formula (3)

It is important for 1,4-bis(bromodifluoromethyl)tetrafluorobenzene (BFTFB) represented by the following Formula (4) to be the monomer of the above-mentioned dimer, to not contain any hydrogen atoms, of fluoro parylene polymers.

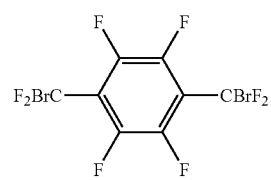

Formula (4)

1,4-bis(dichloromethyl)tetrafluorobenzene (DCMTFB), as shown in the following Formula (5), is a critical precursor for synthesis of the foregoing 1,4-bis(bromodifluoromethyl)tetrafluorobenzene (BFTFB).

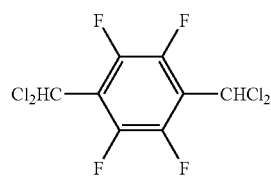

Formula (5)

Nowadays, 1,4-bis(dichloromethyl)tetrafluorobenzene (DCMTFB) is synthesized by reacting 1,2,4,5-tetrafluorobenzene (TFB) with $CHCl_3$, as shown in the following Reaction (I).

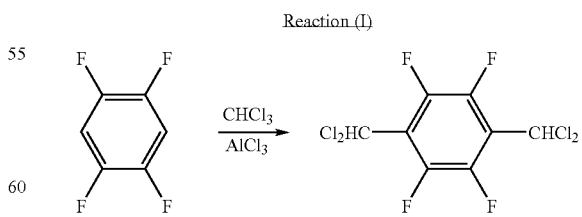

Reaction (I)

However, this method is time-consuming and low-yielding, and needs silica-gel column chromatography to purify the crude product. Hence, this method is unsuitable for mass production.

Therefore, it is desirable to provide a prompt and high-yield method for synthesize 1,4-bis(dichloromethyl)tetrafluorobenzene (DCMTFB), and such method is appropriate for mass production.

SUMMARY OF THE INVENTION

The present invention provides a method for producing 1,4-bis(dichloromethyl)tetrafluorobenzene. This method can reduce the reaction time, simplify the procedures and promote the yield for producing 1,4-bis(dichloromethyl)tetrafluorobenzene. The reaction of the method is shown as the following Reaction (II).

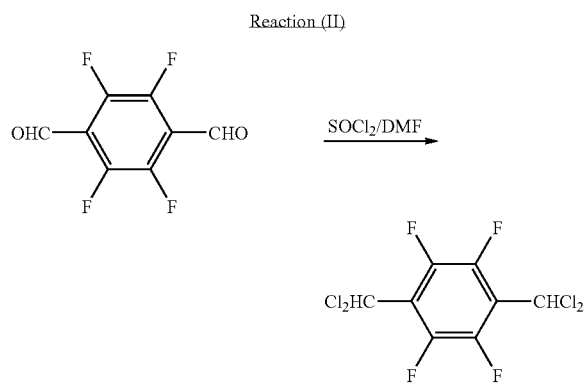

Reaction (II)

The present invention provides a method for producing 1,4-bis(dichloromethyl)tetrafluorobenzene, which comprises the following steps:

(a) mixing tetrafluoroterephthaldehyde, a catalyst and $SOCl_2$ with or without organic solvents to form a mixture, wherein the catalyst belongs to formamides;

(b) heating the mixture;

(c) cooling the mixture, adding the mixture into water slowly, and letting the mixture separate into two layers;

(d) obtaining an organic layer from the layers of the mixture; and (e) purifying the organic layer and removing the organic solvents and the catalyst in the organic layer and affording 1,4-bis(dichloromethyl)-tetrafluorobenzene.

In the method of the present invention, the molar ratio of tetrafluoroterephthaldehyde to $SOCl_2$ is at least more than 2. The molar ratio of tetrafluoroterephthaldehyde to $SOCl_2$ is preferably in the range from 2 to 20, and more preferably in the range from 5 to 8.

In the method of the present invention, the weight ratio of the catalyst to tetrafluoroterephthaldehyde is in the range from 0.1 to 1.0, and preferably in the range from 0.2 to 0.4.

In the method of the present invention, the weight ratio of the organic solvent to tetrafluoroterephthaldehyde is in the range from 0 to 3, and preferably in the range from 1 to 2.

In the method of the present invention, the mixture in the step (b) is heated until the temperature thereof rises to the range from 60 to 130° C., and preferably to the range from 85 to 100° C.

In the method of the present invention, the reaction time of the step (b) is in the range from 2 to 30 hours, and preferably to the range from 4 to 6 hours.

In the method of the present invention, the mixture is cooled in the range from 0 to 60° C. in the step (c), and preferably in the range from 25 to 40° C. so as to avoid the overreaction of hydrolysis.

In the method of the present invention, the mixture can be added into water slowly at 0 to 25° C., and preferably into iced water in the step (c) to avoid the overreaction of hydrolysis.

The method of the present invention can be performed without or with an organic solvent nonreactive to $SOCl_2$. The organic solvent is preferably at least one selected from the group consisting of toluene, chloroform, p-xylene, benzene, dioxane, 1,2-dichloroethane, tetrachloromathane, tetrahydrofuran, nitrobenzene, and o-dichlorobenzene, and more preferably is toluene or benzene.

In the method of the present invention, the catalyst is N,N-dialkylformamide, wherein the alkyl group is a $C_1$~$C_7$ alkyl group. Preferably, the catalyst is N,N-dimethylformamide (DMF), or N,N-diethylformamide (DEF).

In the method of the present invention, the purification of the step (e) preferably comprises the following steps:

(e1) adding an organic solvent and water ($H_2O$) into the organic layer under stirring;

(e2) neutralizing the mixture;

(e3) isolating the organic layer and then concentrating the organic layer; and (e4) cooling the organic layer to obtain a solid product.

In the above-mentioned step (e), the volume ratio of the organic solvent to water is in the range from 1 to 10 in the step (e1), and preferably is 1. The organic solvent can be any organic solvent which can dissolve 1,4-bis(dichloromethyl)tetrafluorobenzene but is not miscible with water, and preferably is dichloromethane in the step (e1). The mixture can be neutralized by any basic solution, and preferably by concentrated ammonia in the step (e2).

Other objects, advantages, and novel features of the invention will become more apparent from the following detailed description when taken in conjunction with the accompanying drawings.

DETAILED DESCRIPTION OF THE PREFERRED EMBODIMENT

Example 1
Preparation of 1,4-bis(dichloromethyl)tetrafluorobenzene (Toluene as the Solvent and N,N-Dimethylformamide as the Catalyst)

Tetrafluoroterephthaldehyde (TFTPA, 15.45 g), N,N-dimethylformamide (DMF, 3.01 g), and toluene (15.01 g) were added into a 250 mL three-necked reactor equipped with a temperature probe, a condenser and an aeration tube. Under nitrogen atmosphere, $SOCl_2$ (63.37 g) was slowly added into the flask via the channel for the temperature probe by a feed hopper. After the feed hopper was removed, the flask was reequipped with the temperature probe. The reaction mixture was heated in an oil bath under stirring while the aeration of nitrogen was closed, and it was refluxed at 85~95° C. for 2 hours until gas chromatography (GC) analysis informed that the reaction was completed. After the reaction mixture was cooled to room temperature, iced water was slowly introduced thereto to hydrolyze residual $SOCl_2$. The reaction mixture was stood for a while and the aqueous layer was removed. Subsequently, appropriate amounts of dichloromethane (DCM) and $H_2O$ (the volume ratio of DCM to $H_2O$=1/1) were added into the remaining organic layer. The pH value of the mixture was adjusted to 7.0 by concentrated ammonia (conc. $NH_{3(aq)}$). Then, the organic phase was isolated, washed by water, dehydrated by anhydrous magnesium sulfate, and concentrated to remove DCM, toluene, and DMF. Finally, the resultant was cooled to room temperature so that the crude product (22.23 g, crude yield: 93.8%) was obtained. The crude product was recrystallized in n-heptane to afford 13.33 g of the crystal product. The residual n-heptane solution was evaporated, and then recrystallized once again to obtain 6.28 g of the crystal product. The total quantity of recrystallization twice amounted to 19.61 g of the crystal product (the yield: 82.75%).

Data of Chemical Analyses:

(a). Mass spectrum: $M^+$=316.

(b). $^1$H NMR (CDCl$_3$; external standard: TMS) chemical shift (δ): 6.90 ppm (s, 2H).

(c). $^{19}$F NMR (CDCl$_3$; external standard: CFCl$_3$) chemical shift (δ): −139.37 ppm (s, 4F).

(d). $^{13}$C NMR (CDCl$_3$; external standard: TMS) chemical shift (δ): 143.45 ppm (d, $J_{C-F}$=257 Hz, 4 Aromatic C), 120.72 ppm (s, 2 Aromatic C), 58.26 ppm (s, 2 Aliphatic C).

Examples 2 to 16

Preparations of 1,4-bis(dichloromethyl)-tetrafluorobenzene

Examples 2 to 16 were performed in the manner the same as Example 1. However, the amounts of the reagents and the solvent, the reaction conditions, and the yields of the products are listed in Table 1.

Examples 1 to 16 illustrate that the solvent can be toluene, chloroform, p-xylene, benzene, dioxane, 1,2-dichloroethane, tetrachloromathane, tetrahydrofuran, nitrobenzene, or o-dichlorobenzene, and the catalyst is formamides most preferably.

Comparative Example

Conventional Preparation of 1,4-bis(dichloromethyl)tetrafluorobenzene

Comparative Example is a conventional method of producing 1,4-bis(dichloromethyl)tetrafluorobenzene, in which 1,2,4,5-tetrafluorobenzene (TFB) is reacted with CHCl$_3$ to yield 1,4-bis(dichloromethyl)tetrafluorobenzene. This method is detailed in the following.

1,2,4,5-tetrafluorobenzene (TFB, 3.77 g), anhydrous AlCl$_3$ (20.34 g), and CHCl$_3$ dehydrated by NaH as the solvent were added into a 100 mL reactor. The mixture was heated in an oil bath under stirring and refluxed for 24 hours. Subsequently, the mixture was added into iced water slowly to hydrolyze residual AlCl$_3$. The mixture was extracted with chloroform, and then the organic phase was washed by water, dehydrated by anhydrous magnesium sulfate, and concentrated to obtain the crude product. The crude product was purified by silica-gel column chromatography using n-hexane as the eluent, and recrystallized with n-hexane to obtain 1,4-bis(dichloromethyl)tetrafluorobenzene (yield: 59.33%).

Table 2 shows the drawbacks and advantages of the present Comparative Example compared with Example 1.

Based on Table 2, the cost of Example 1 is 1.5-fold more than that of the Comparative Example. However, the method of Example 1 can reduce the reaction time, simplify the procedures, have a larger reactor capacity and promote the yield for producing 1,4-bis(dichloromethyl)tetrafluorobenzene. These aspects of Example 1 are better than those of the Comparative Example.

Although the present invention has been explained in relation to its preferred embodiment, it is to be understood that many other possible modifications and variations can be made without departing from the scope of the invention as hereinafter claimed.

TABLE 1

The reaction conditions and the results in Examples 1 to 16

| Example | TFTPA (g) | SOCl$_2$ (g) | Catalyst | (g) | Solvent | (g) | Reaction temperature (°C.) | Reaction times (hours) | DCMTFB (g) | Yield (%) | Remarks |
|---|---|---|---|---|---|---|---|---|---|---|---|
| 1 | 15.45 | 63.37 | DMF | 3.01 | Toluene | 15.01 | 85-95 | 2.0 | 19.61 | 82.75 | |
| 2 | 15.44 | 55.61 | DMF | 3.01 | Chloroform | 25.35 | 73-79 | 6.0 | 16.01 | 67.59 | |
| 3 | 15.46 | 55.73 | DMF | 3.02 | p-Xylene | 14.81 | 90-104 | 3.0 | 14.26 | 60.13 | |
| 4 | 15.46 | 56.51 | DMF | 3.00 | Benzene | 14.97 | 80-88 | 4.25 | 19.24 | 81.13 | |
| 5 | 15.46 | 55.57 | DMF | 3.01 | Acetonitrile | 13.29 | 77-83 | 6.0 | 4.93 | 20.79 | *1 |
| 6 | 15.45 | 55.45 | DMF | 3.01 | Dioxane | 17.55 | 91-99 | 4.0 | 17.49 | 73.80 | |
| 7 | 15.45 | 58.60 | DMF | 3.01 | 1,2-Dichloroethane | 21.18 | 81-87 | 4.0 | 17.25 | 72.79 | |
| 8 | 15.45 | 55.57 | DMF | 3.01 | Tetrachloromathane | 27.34 | 75-81 | 6.0 | 16.09 | 67.89 | |
| 9 | 15.45 | 55.45 | DMF | 3.03 | Tetrahydrofuran | 15.29 | 80-90 | 3.0 | 14.47 | 61.05 | |
| 10 | 15.45 | 55.87 | DMF | 3.01 | Nitrobenzene | 20.44 | 106-108 | 2.0 | 13.62 | 57.47 | |
| 11 | 15.45 | 55.80 | DMF | 3.01 | o-Dichlorobenzene | 22.24 | 94-100 | 2.0 | 17.41 | 73.45 | |
| 12 | 15.45 | 55.52 | DMF | 3.02 | — | — | 85-90 | 3.0 | 6.38 | 26.92 | |
| 13 | 15.45 | 55.93 | DMF | 3.01 | — | — | 85-90 | 29.0 | 2.16 | 9.12 | *2 |
| 14 | 15.44 | 55.71 | DMAC | 3.00 | Toluene | 15.00 | 84-97 | 6.0 | — | — | *3 |
| 15 | 15.44 | 55.45 | NMP | 3.00 | Toluene | 15.00 | 85-93 | 5.0 | — | — | *4 |
| 16 | 15.44 | 56.74 | DEF | 3.01 | Toluene | 15.01 | 85-97 | 4.0 | 18.75 | 79.17 | |

DMF: N,N-dimethylformamide
DMAC: dimethylacetamide
NMP: N-methylpyrrolidone
DEF: N,N-diethylformamide
*1: Solution turned black.
*2: TFTPA was of poor purity.
*3: Solution turned black and only little product was obtained.
*4: Solution turned black and only little product was obtained.

TABLE 2

The drawbacks and advantages of the present Comparative Example compared with Example 1

| | Example 1 | Comparative Example |
|---|---|---|
| Reaction Time | 2 hours | 24 hours |
| Yield | 82.75% | 59.33% |
| Reactor Capacity | Large | Small |
| Preliminary Process for Solvent | Simple and Convenient | Complex |
| Purification of Product | Recrystallization | Column Chromatography |
| Cost of Material (For Synthesis of 1 kg DCMTFB) | Expensive (NTD: 128,000) | Cheap (NTD: 51,000) |

What is claimed is:

1. A method for producing 1,4-bis(dichloromethyl)-tetrafluorobenzene, comprising the following steps:
   (a) mixing tetrafluoroterephthaldehyde, a catalyst and $SOCl_2$ with or without organic solvents to form a mixture, wherein the catalyst is formamides;
   (b) heating the mixture;
   (c) cooling the mixture, adding the mixture into water slowly, and letting the mixture separate into two layers;
   (d) obtaining an organic layer from the layers of the mixture; and
   (e) purifying the organic layer and removing the organic solvents and the catalyst in the organic layer and affording 1,4-bis(dichloromethyl)-tetrafluorobenzene.

2. The method as claimed in claim 1, wherein the molar ratio of tetrafluoroterephthaldehyde to $SOCl_2$ is in the range from 2 to 20.

3. The method as claimed in claim 1, wherein the weight ratio of the catalyst to tetrafluoroterephthaldehyde is in the range from 0.1 to 1.0.

4. The method as claimed in claim 1, wherein the weight ratio of the organic solvent to tetrafluoroterephthaldehyde is in the range from 0 to 3.

5. The method as claimed in claim 1, wherein the mixture is refluxed by heating in the step (b).

6. The method as claimed in claim 1, wherein the mixture in the step (b) is heated until the temperature thereof rises to the range from 60 to 130° C.

7. The method as claimed in claim 1, wherein the reaction time of the step (b) is in the range from 2 to 30 hours.

8. The method as claimed in claim 1, wherein the mixture is cooled in the range from 0 to 60° C. in the step (c).

9. The method as claimed in claim 1, wherein the mixture is added to iced water slowly in the step (c).

10. The method as claimed in claim 1, wherein the organic solvent is at least one selected from the group consisting of toluene, chloroform, p-xylene, benzene, dioxane, 1,2-dichloroethane, tetrachloromathane, tetrahydrofuran, nitrobenzene, and o-dichlorobenzene.

11. The method as claimed in claim 1, wherein the catalyst is N,N-dialkylformamide, and the alkyl group is a $C_1$~$C_7$ alkyl group.

12. The method as claimed in claim 1, wherein the catalyst is N,N-dimethylformamide (DMF), or N,N-diethylformamide (DEF).

13. The method as claimed in claim 1, wherein the step (e) comprises the following steps:
   (e1) adding an organic solvent and water ($H_2O$) into the organic layer under stirring;
   (e2) neutralizing the mixture;
   (e3) isolating the organic layer and then concentrating the organic layer; and
   (e4) cooling the organic layer to obtain a solid product.

14. The method as claimed in claim 13, wherein the volume ratio of the organic solvent to water is in the range from 1 to 10 in the step (e1).

15. The method as claimed in claim 13, wherein the organic solvent is dichloromethane in the step (e1).

16. The method as claimed in claim 13, wherein the mixture is neutralized by concentrated ammonia in the step (e2).

* * * * *